United States Patent

Chu et al.

Patent Number: 5,900,552
Date of Patent: May 4, 1999

[54] INWARDLY DIRECTED WAVE MODE ULTRASONIC TRANSDUCER, GAS ANALYZER, AND METHOD OF USE AND MANUFACTURE

[75] Inventors: Ching Chu, Madison; Neil D. Roiland, Deerfield, both of Wis.

[73] Assignee: Ohmeda Inc., Liberty Corner, N.J.

[21] Appl. No.: 08/828,441

[22] Filed: Mar. 28, 1997

[51] Int. Cl.[6] ............................ G01H 3/00; G01N 29/02
[52] U.S. Cl. ........................... 73/632; 73/24.06; 310/369
[58] Field of Search ............................ 73/24.01, 24.06, 73/24.05, 24.03, 632, 24.04; 310/348, 367, 369; 367/159

[56] References Cited

U.S. PATENT DOCUMENTS

| | | |
|---|---|---|
| 2,874,564 | 2/1959 | Martin et al. . |
| 3,343,403 | 9/1967 | Romani et al. . |
| 3,543,059 | 11/1970 | Angelhoff ............................ 310/369 X |
| 3,816,774 | 6/1974 | Ohnuki et al. ....................... 310/369 X |
| 4,280,183 | 7/1981 | Santi . |
| 4,663,977 | 5/1987 | Vander Heyden . |
| 4,706,229 | 11/1987 | Congdon ............................ 310/369 X |
| 4,859,897 | 8/1989 | Massa ................................. 310/369 X |
| 4,938,066 | 7/1990 | Dorr . |
| 5,060,506 | 10/1991 | Douglas . |
| 5,060,514 | 10/1991 | Aylsworth . |
| 5,285,677 | 2/1994 | Oehler . |
| 5,392,635 | 2/1995 | Cadet et al. . |
| 5,452,621 | 9/1995 | Aylesworth et al. . |

FOREIGN PATENT DOCUMENTS

| | | |
|---|---|---|
| 2 027 198 | 2/1980 | United Kingdom . |
| 2 215 049 | 9/1989 | United Kingdom . |
| WO 92/03724 | 3/1992 | WIPO . |

OTHER PUBLICATIONS

Kielczynski, et al, IIEEE Transactions on Ultrasonics Ferroelectrics and Frequency Control vol. 37, No. 1, pp. 38–43, 1990, "Ring Piezoelectric Transducers Radiating Ultrasonic Energy into the Air".

Baldes, et al "Proceedings of Mayo Clinic", vol. 14, 1939, pp. 588–592.

Stott, "Rev. Sci. Instr." vol. 28, 1957, pp. 914–915.

Faulconer, Jr., et al "Anesthesiology" vol. 11, May 1950, No. 3, pp. 265–278.

Amp Inc. "Piezo Film Sensors Technical Manual", Revised Dec. 1993, 63 pages.

*Primary Examiner*—Michael Brock
*Attorney, Agent, or Firm*—Roger M. Rathbun

[57] ABSTRACT

An ultrasonic transducer is disclosed for emitting an ultrasonic wave radially inward. The transducer is constructed with a strip of piezoelectric material laminated with a pair of electrically conductive metal layers that are conductively isolated from one another. In a preferred embodiment, the strip of piezoelectric material is formed in a cylindrical shape and with continuous sinusoidal ripples along the circumference. The sinusoidal ripples are designed to emit a specific wave length of a desired frequency. The radius of the sinusoidal wave is based on material characteristics and the desired resonance frequency. The invention discloses various methods and apparatus for constructing and maintaining the transducer sinusoidal shape. One method includes attachment of a pair of rigid end caps on the laminated piezoelectric material, and another discloses weaving the laminated piezoelectric material through a nonconductive mesh cage, and yet another includes adhesively attaching the transducer to a housing. The invention also includes an application of the above described transducers in a gas analyzer having an internal chamber in which the transducer is arranged. The method of analyzing gas includes passing the gas through the internal chamber and across the surface of the transducer, energizing the transducer to emit an ultrasonic wave into the passing gas toward the center of the transducer. The ultrasonic wave is reflected from a pressure center and sensed by the same transducer that emitted the wave. The invention also includes a method of manufacturing the transducer with sinusoidal ripples to accomplish an emission of desired frequency.

36 Claims, 7 Drawing Sheets

INWARDLY DIRECTED WAVE MODE ULTRASONIC TRANSDUCER, GAS ANALYZER, AND METHOD OF USE AND MANUFACTURE

BACKGROUND OF THE INVENTION

The present invention relates generally to ultrasonic transducers, and more particularly to a cylindrical or circular ultrasonic transducer designed to emit ultrasonic sound waves radially inward and to sense reflected ultrasonic waves from a pressure center at or near the center of the ultrasonic transducer. One particular application for the transducer of the present invention is in a gas analyzer that would be particularly useful in the medical field. A method of analyzing gas and a method of manufacturing the ultrasonic transducer are also disclosed.

Acoustical monitoring of gas can employ ultrasound having a frequency ranging from a few kHz to 10 MHZ. Acoustical techniques have been extensively used for gas flow monitoring. Most recently, efforts have turned to developing acoustical cells and processes which can determine the concentration of a component of a binary gas mixture. In general, acoustical concentration analysis of a gas mixture is performed by measuring the speed with which sound waves propagate through a gas mixture. Because the speed at which the sound waves travel through a gas is related to molecular weight, the concentration of a component of a gas mixture can be accurately determined.

Ultrasonic transducers that transmit and receive ultrasonic sound waves are common in the prior art, and have been commonly used in gas analyzers and gas flow meters. Typically, either two transducers are placed within a tube, or cylinder housing, one at each end, or a single transducer is placed at one end and an acoustical reflector at the other. For example, just a few include U.S. Pat. Nos. 5,452,621, 5,285,677, 4,938,066, 4,280,183, and 2,874,564, all of which either use multiple transducers, one for a transmitter and one for a receiver, or a single transducer and at least one separate reflector. This basic arrangement generally results in a low signal to noise ratio (i.e. high noise), an undesirable high detraction of emitted waves, and high structure reverberation. Much of the cited prior art attempts to correct these physical flaws of the transducers and the transducer arrangement through the use of sophisticated controls and processors.

It would therefore be desirable to eliminate these physical problems up-front at the source rather than at the back end with error correction controls.

Other types of methods and apparatus have been used as well for determining the concentration of a gas within a particular specimen, such as the concentration of oxygen as used in medical applications. For example, the concentration of oxygen has been detected by passing a gas over a fuel cell terminal that analyzes the gas being measured by generating a signal as a result of exposure of the gas to the cell terminal. Another, tests the consumption of oxygen in a test specimen and extrapolates that percentage to the overall gas sample. Another uses expendable chemical cells. Many others exist, but are generally unacceptable because they either interfere with the flow of the gas to be analyzed, have finite life due to cell consumption, require constant calibration, or are cost prohibitive.

Therefore, it would also be desirable to have an inwardly directed wave mode ultrasonic transducer, gas analyzer, and method of use and manufacture that solves all the aforementioned problems and could provide a high signal to noise ratio, has a wide emission surface area of for low defraction, and is relatively inexpensive to manufacture.

SUMMARY OF THE INVENTION

The present invention accomplishes the foregoing by providing an ultrasonic transducer that is capable of radiating an ultrasonic wave radially inward from the transducer and overcomes the aforementioned problems. The transducer is applied in a gas analyzer for passing a gas therethrough and analyzing its constituents.

In accordance with one aspect of the invention, an inwardly directed wave mode ultrasonic transducer is constructed with a strip of piezoelectric material formed in a substantially cylindrical shape and has a pair of electrically conductive metal layers laminated on the inside and outside surfaces of the piezoelectric material. The metal layers are spaced apart to conductively isolate one from the other. A pair of end caps are attached at each edge of the cylindrically shaped transducer to provide rigidity and maintain its shape. The transducer is constructed to create and maintain a hollow center and to emit a substantially cylindrical ultrasonic wave radially inward.

In accordance with another aspect of the invention, the previously described ultrasonic transducer is formed with multiple ripples orientated parallel to a central axis of a cylindrically shaped transducer. The ripples are substantially sinusoidal along a circumference of the transducer. The radius of the sinusoidally shaped ripples define an operational frequency of the transducer. The transducer can be constructed to emit a frequency of choice by calculating the radius of the sinusoid using the desired frequency and the known properties of the piezoelectric material.

In accordance with another aspect of the invention, an ultrasonic transducer is disclosed in which a strip of piezoelectric material has an electrically conductive metal layer laminated on each side. The combination is weaved through a series of vertical members and openings in a nonconductive mesh cage to form the sinusoidal ripples previously described. This transducer incorporating a strip of piezoelectric material weaved through the nonconductive mesh cage is also constructed to create and maintain a hollow center such that it is capable of radiating the ultrasonic wave radially inward.

In accordance with yet another aspect of the invention, an ultrasonic transducer having the above described capabilities is constructed of a strip of piezoelectric material having an electrically conductive metal layer laminated on both its surfaces such that each is electrically isolated from the other. The strip is attached or adhered to a substantially cylindrical hollow housing thereby maintaining a hollow center and radiating an ultrasonic wave radially inward. The strip of piezoelectric material can be formed with the sinusoidal ripples previously described to emit ultrasonic waves at a desired frequency. The transducer can be attached to the housing with adhesive on each sinusoidal peak in contact with the housing. The transducer can be attached to the inside surface or the outside surface of the housing.

In accordance with yet another aspect of the invention, a method of producing such an ultrasonic transducer is disclosed including the steps of determining the modulus of elasticity and the density of the piezoelectric material chosen, determining a desired operating frequency of the ultrasonic transducer, and calculating an optimal radius of a sinusoidal ripple based on the modulus of elasticity and the density of the piezoelectric material, along with the desired operating frequency. The piezoelectric material is then shaped to form a continuous full wave sinusoid, wherein each of the half waves of the sinusoid has a radius which is substantially equal to the calculated optimal radius.

Another aspect of the invention includes the application of any of the aforementioned transducers in a gas analyzer. The gas analyzer has a housing with a gas inlet, a gas outlet, and an internal chamber in communication with the gas inlet and gas outlet. An ultrasonic transducer, according to the invention, is arranged in the internal chamber of the housing to allow gas flow therethrough. In operation, an ultrasonic emission from the ultrasonic transducer converges radially inward toward a pressure center in the internal chamber, and once converged, will reflect back to the ultrasonic transducer, which in turn senses the returned, reflected ultrasonic wave.

Accordingly, a method of analyzing gas is also disclosed. According to the invention, the method includes passing a gas to be analyzed through an inside surface of a substantially cylindrical shaped ultrasonic transducer, energizing the ultrasonic transducer and radiating an ultrasonic cylindrical wave into the passing gas and toward a center of the cylindrical shaped transducer. The ultrasonic cylindrical wave detects characteristics of the gas to be analyzed, and the transducer senses the reflected ultrasonic cylindrical wave containing acoustical characteristics indicative of the detected characteristics of the gas with the same cylindrical shaped ultrasonic transducer that emitted the original wave.

Therefore, it is readily apparent, in the most general sense an ultrasonic device is disclosed for producing a radially inward directed ultrasonic wave which will be reflected from a pressure center near the interior center of the device. The pressure center will reflect the ultrasonic wave back to the ultrasonic device which can then sense the returned wave. The device includes a means for emitting an ultrasonic wave of a desired frequency, wherein the means is also for sensing a returned ultrasonic wave. The emitted ultrasonic wave is directed radially inward from the means for producing, and the returned ultrasonic wave is reflected from a pressure center formed by the inwardly directed ultrasonic wave. The same means emits the ultrasonic wave and senses the returned ultrasonic wave. By forming the means for emitting and sensing with a plurality of ripple means therein, the frequency emitted can be predetermined and controlled.

Various other features, objects and advantages of the present invention will be made apparent from the following detailed description and the drawings.

BRIEF DESCRIPTION OF THE DRAWING

The drawings illustrate the best mode presently contemplated for carrying out the invention.

In the drawings.

DETAILED DESCRIPTION OF THE INVENTION

Figure 1:
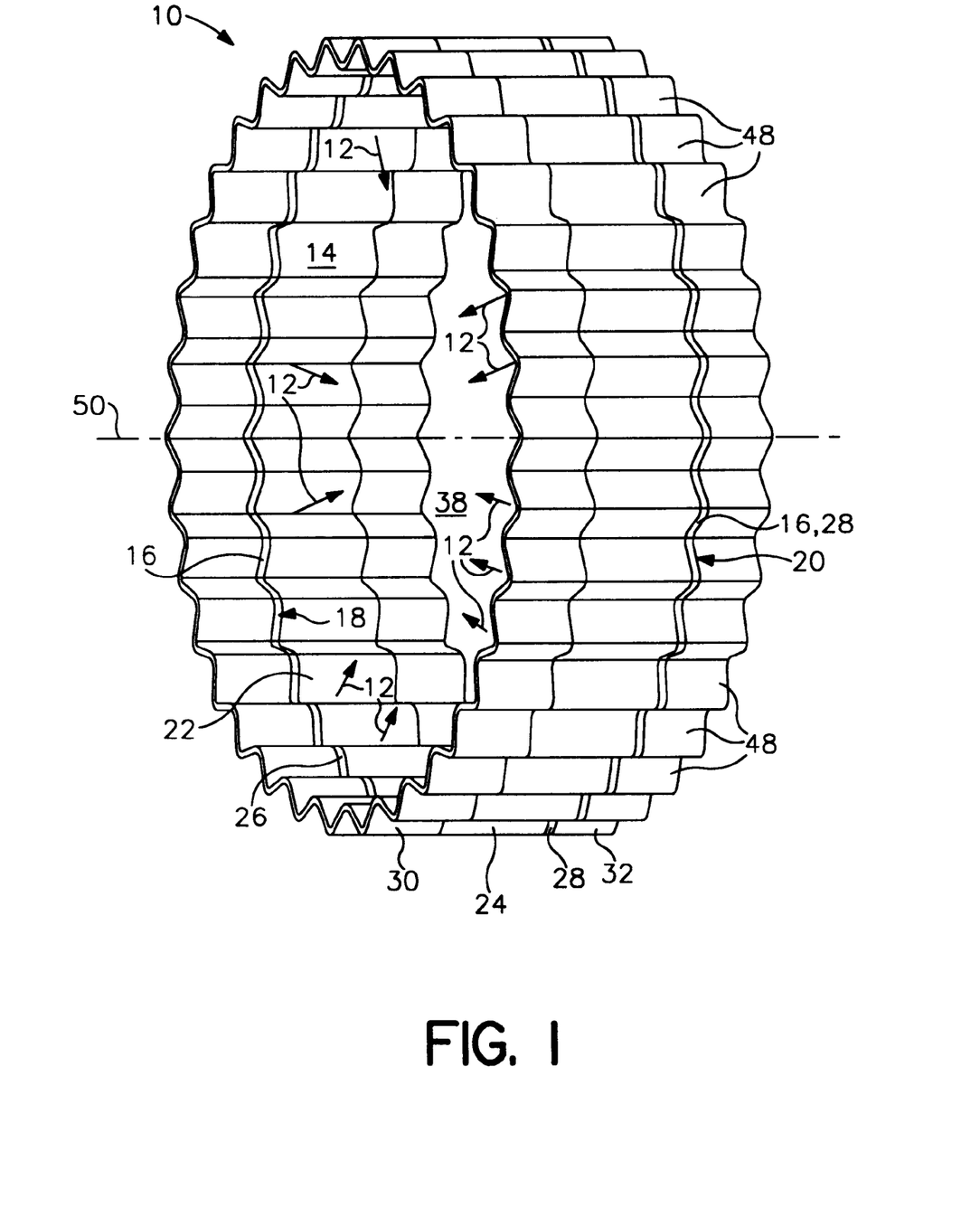
FIG. 1 is a perspective view of an ultrasonic transducer according to the present invention.

Referring to FIG. 1, an ultrasonic transducer 10, shown in perspective view, is constructed according to the present invention to emit an ultrasonic wave radially inward as illustratively indicated by arrows 12. The wave is radiated from an inner circumference 14. The ultrasonic transducer of the present invention is generally referred to as an inwardly directed waved mode transducer, and the ultrasonic transducer 10 of FIG. 1, is more specifically referred to as a cylindrical wave mode ultrasonic transducer since the resulting ultrasonic wave is substantially cylindrical in shape.

The ultrasonic transducer 1 0 has an underlying strip of piezoelectric material 16 which is viewed through gaps 18 and 20 formed by a pair of electrically conductive metal layers 22 and 24 covering the piezoelectric material 16. The strip of piezoelectric material 16 has an inside surface 26 and an outside surface 28 and is formed in a substantially cylindrical shape. The pair of electrically conductive metal layers 22 and 24 are preferably laminated on the inside surface 26 and the outside surface 28 of the piezoelectric material 16 and are spaced apart to form the gaps 18 and 20 on each of the surfaces between the electrically conductive metal layers 22 and 24. The gaps 18 and 20 run parallel with one another along a perimeter of the cylindrically shaped strip of piezoelectric material 16.

Figure 3:
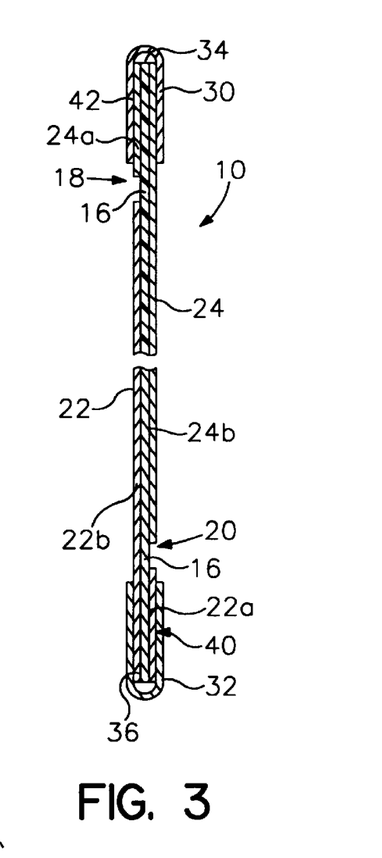
FIG. 3 is a side cross-sectional view of the component part of FIG. 2 taken along line 3—3 of FIG. 2.

As is indicated in FIG. 1, and best shown in FIG. 3, a pair of end caps 30 and 32 are folded over and attached to each edge surface 34 and 36 of the cylindrically shaped ultrasonic transducer 10. As is evident in FIG. 1, the transducer 10 is constructed to create and maintain a hollow center 38 such that the ultrasonic transducer 10 of the present invention is capable of radiating, or emitting, a substantially cylindrical ultrasonic wave radially inward as shown by arrows 12.

Referring to FIG. 3, the electrically conductive metal layers 22 and 24 have a relatively narrow portion or layer 22a and 24a covering a minority of one side of the piezoelectric material 16, and a relatively wider layer 22b and 24b covering a majority of the opposite side of the piezoelectric material 16. Each of the electrically conductive metal layers 22 and 24 act as an electrode for the transducer 10. The end caps are rigid and provide stability to the transducer to maintain a desired shape. For example, the cylindrical shape shown in FIG. 1 is maintained with the rigid end caps. The end caps 30 and 32 may be metallic and electrically conductive to conductively connect the electrically conductive metal layers 22 and 24 and the piezoelectric material 16, to an external energy source, as will later be described with reference to FIG. 18.

Figure 2:
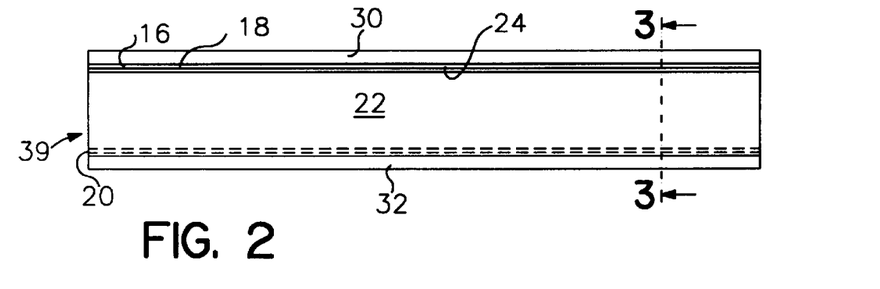
FIG. 2 is a top view of a component part of the device of FIG. 1.

Preferably, the piezoelectric material is of the polyvinylidene fluoride (PVDF) type and is readily available in strips with the electrically conductive metal layers 22 and 24 laminated thereon. The piezoelectric material 16 is shown laid out end to end in FIG. 2 with electrically conductive metal layer 22 and gap 18 facing upward and the majority of the electrically conductive metal layer 24 facing downward with a narrow portion wrapped over the top of the piezoelectric material 16. End cap 30 is placed over the top edge. Gap 20 is shown in shadow from the underside and end cap 32 is placed on a lower edge of the laminated layer 22 and piezoelectric material 16. In the preferred embodiment of FIG. 1, the strip of piezoelectric material of FIG. 2 is formed with a plurality of ripples 48, FIG. 1, orientated parallel to a central axis 50 of the cylindrically shaped transducer 10. The ripples 48 are continuous along a circumference of the transducer 10 and are substantially sinusoidal. It has been found that a radius of the sinusoid defines the operational frequency of the ultrasonic transducer 10. In this manner, the transducer can be designed to emit a desired frequency by forming the piezoelectric material with the correct radius. However, other shapes can be equivalently substituted for the sinusoid shape that is shown and described herein. As one example, the transducer can be constructed with triangular shaped ripples with similar results. The sinusoidal shape is preferred because of ease of manufacture and design.

It is contemplated that it will be desirable to emit frequencies in a specific bandwidth. Adding the above mentioned ripples to the ultrasonic transducer can achieve this end. Accordingly, the present invention includes a method of producing an ultrasonic transducer capable of emitting an ultrasonic wave radially inward. The method is accomplished by first determining a modulus of elasticity and density of the piezoelectric material to be used. The next step in producing an ultrasonic transducer according to this method is calculating an optimal radius (r) of a sinusoidal ripple 48 based on the modulus of elasticity (Y) and the density ( ) of the piezoelectric material 16, along with a desired operating frequency ($f_r$). Then, the piezoelectric material 16 must be shaped to form a continuous full wave sinusoid, wherein each of the half waves of the sinusoid has a radius substantially equal to the calculated optimal radius (r).

For an example, in one preferred embodiment using PVDF having a density of elasticity ( ) of $1.770 \times 10^3$ kg/m$^3$ and a modulus of elasticity (Y) of $4.5 \times 10^9$ N/m$^2$, a desired operating frequency of the ultrasonic transducer can be determined. As an example, for a resonance frequency ($f_r$) of 126.88 kHz the resulting radius of the sinusoidal ripple must be 2 mm. This result is calculated using the equation:

$$r = \frac{1}{2\pi f_r} \sqrt{\frac{Y}{\rho}}$$

Figure 4:
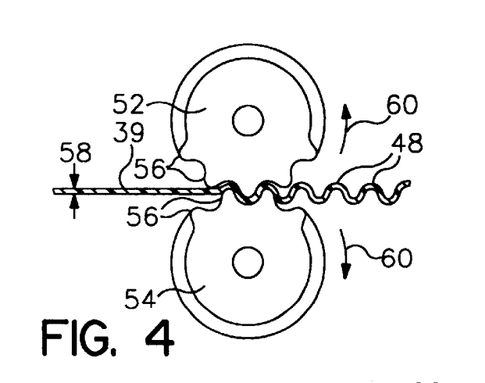
FIG. 4 is a side view demonstrating the method of manufacture of the device of FIG. 1.

One method of accomplishing the sinusoidal shaping is shown with reference to FIG. 4. A pair of geared rollers 52 and 54 are selected having a series of teeth 56 with a pitch and diameter based on the calculated optimal radius (r) and are arranged such that the teeth of one geared roller 52 mesh with the teeth of the second geared roller 54 in a close relation and controlled distance in accordance with the thickness 58 of the assembled strip described with reference to FIGS. 2 and 3. The previously described step of shaping the piezoelectric material to form a continuous full wave sinusoid is further defined as feeding the assembled planar strip 39 through the meshed pair of gears 52 and 54, as indicated by arrow 60 in FIG. 4, to form the plurality of ripples 48 that make up the continuous full wave sinusoid.

Figure 5:
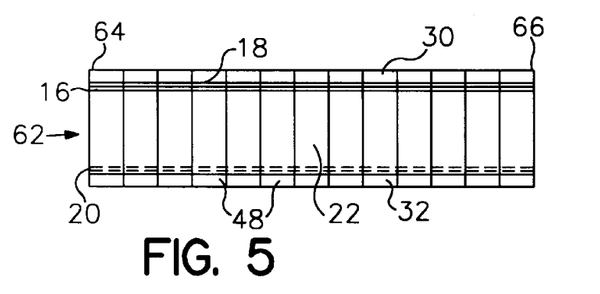
FIG. 5 is a top view of the component part of FIG. 2 incorporating the process shown in FIG. 4.
Figure 6:
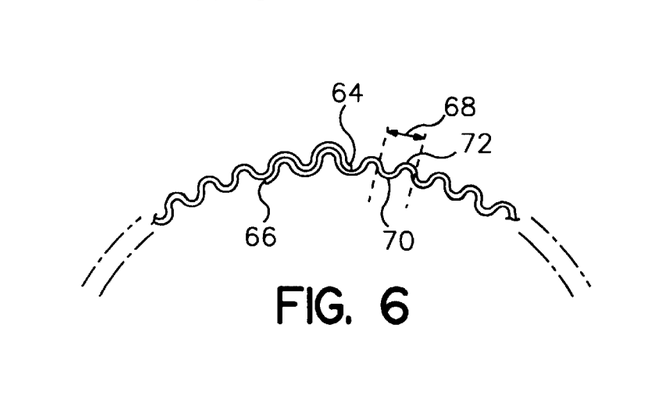
FIG. 6 is a partial top view of FIG. 1.

FIG. 5 shows the resulting assembled rippled strip 62 having a plurality of ripples 48 formed in the process described with reference to FIG. 4. As is evident from a comparison of FIG. 2 and 5, after proceeding through the process of FIG. 4, the resulting rippled strip 62 appears shorter than the original planar strip 39 because of the plurality of ripples therein. To complete the process, the rippled strip ends 64 and 66 are brought around and overlapped as shown in FIG. 6, and bonded to one another to form the cylindrical ultrasonic transducer of FIG. 1. Bonding is accomplished by any conventional manner, such as welding, soldering, or crimping. FIG. 6 also shows what is defined herein as a full wave sinusoid 68 defined to have two peaks 70 and 72.

Figure 7:
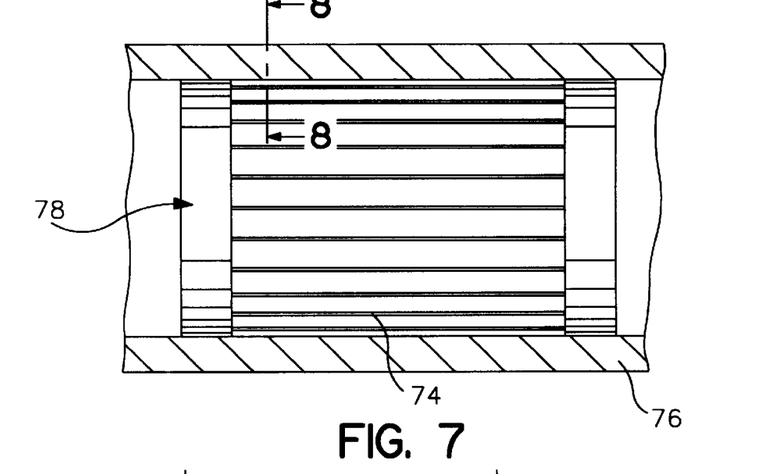
FIG. 7 is a side cross-sectional view of another embodiment of the ultrasonic transducer of the present invention.

FIG. 7 shows another preferred embodiment in which a cylindrical ultrasonic transducer 74 is situated in a housing 76 and is constructed to create and maintain a hollow center 78, thereby being capable of radiating, or emitting, an ultrasonic wave radially inward to a center of housing 76 and ultrasonic transducer 74.

Figure 8:
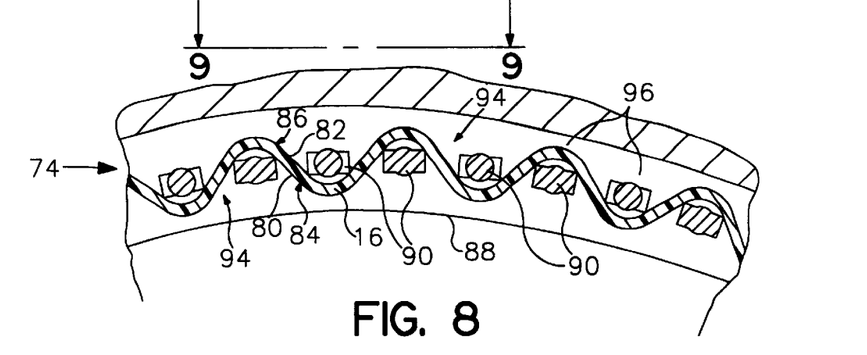
FIG. 8 is a cross-sectional view of a portion of FIG. 7 taken along line 8—8 of FIG. 7.
Figure 9:
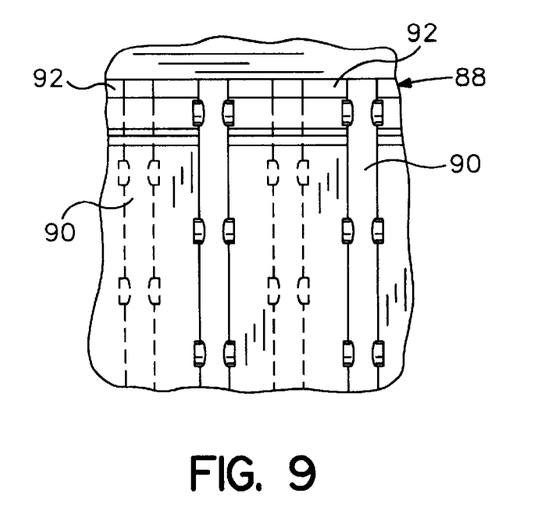
FIG. 9 is a partial side view of FIG. 8 taken along line 9—9 of FIG. 8.

FIG. 8 shows a detailed view of the ultrasonic transducer 74 of FIG. 7 taken along line 8—8. Ultrasonic transducer 74 has a strip of piezoelectric material 16 having a pair of electrically conductive metal layers 80 and 82 on an inside surface 84 and an outside surface 86, respectively, such that each is electrically isolated from one another. Here, there is no need to form gaps on the side surfaces. Gaps are formed on the edge surfaces to maintain each metal layer at its own potential. A nonconductive mesh cage 88 is provided for weaving the piezoelectric material 16 therethrough as shown in FIGS. 8 and 9. The nonconductive mesh cage 88 has multiple vertical members 90 and multiple horizontal members 92. The nonconductive mesh cage also has multiple vertical openings 94 between the vertical members 90 to allow the weaving of the strip of piezoelectric material 82 between the vertical members 90. The horizontal members 92 maintain the vertical position of the piezoelectric material 16 in the mesh cage 88.

The operational frequency, or the resonance frequency, of the ultrasonic transducer 74 of FIGS. 7–9 is determined the same as previously described but is accomplished through a spacial frequency 96 of the vertical members 90 and the vertical openings 94 which define the radius of the sinusoidal radius as is evident from FIG. 8.

Figure 10:
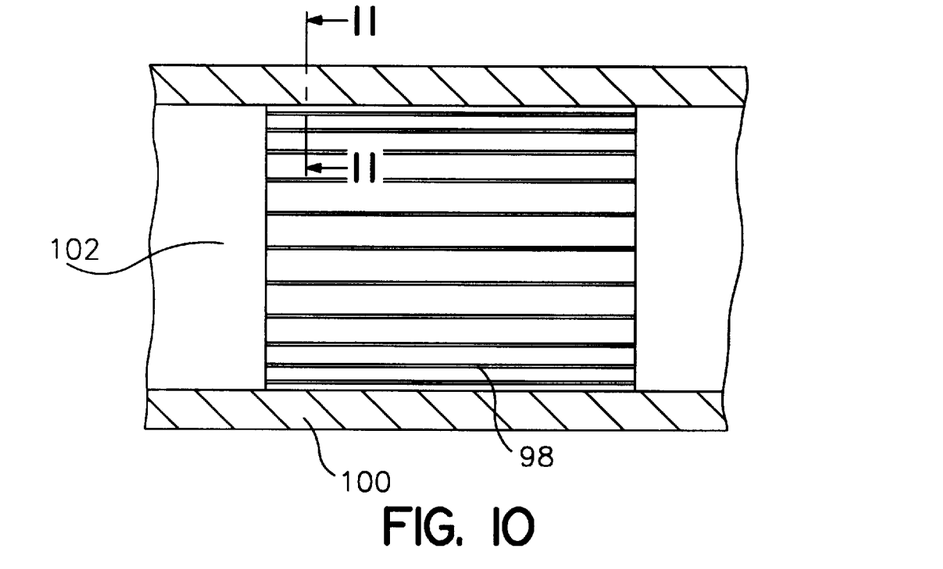
FIG. 10 is a side cross-sectional view of another embodiment of the ultrasonic transducer of the present invention.

Referring to FIG. 10, yet another embodiment is shown in which a cylindrical ultrasonic transducer 98 is attached to a housing 100. In this embodiment, the shape of the ultrasonic transducer is maintained by positive attachment to housing 100, whereas rigidity in the ultrasonic transducer 74 of FIG. 7 was provided by the mesh cage, and the rigidity of the ultrasonic transducer 10 of FIG. 1 was provided by the end caps 30 and 32 to maintain the cylindrical shape. Referring back to FIGS. 10–12, the ultrasonic transducer 98, as previously described with reference to FIG. 8, has a strip of piezoelectric material 16 laminated with a pair of electrically conductive metal layers 80 and 82 on an inside surface 84 and on an outside surface 86, respectively, such that each is electrically isolated from the other.

Figure 11:
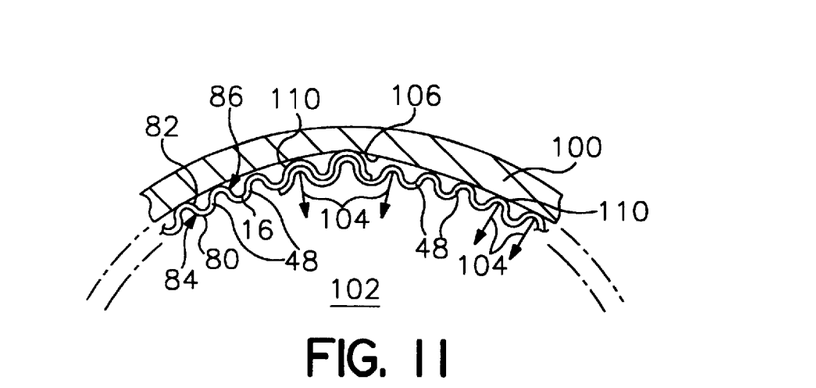
FIG. 11 is a cross-sectional view of a portion of FIG. 10 taken along line 11—11 of FIG. 10.
Figure 12:
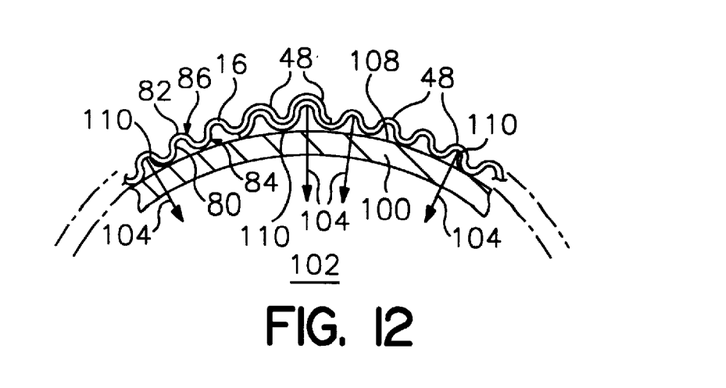
FIG. 12 is a cross-sectional view, similar to FIG. 11, of another embodiment.

A substantially cylindrical housing 100 is provided for mounting the finished strip thereon. The housing has a hollow center 102 and the transducer 98 is attached to the housing to create and maintain a hollow center in the transducer such that it is capable of radiating, or emitting, the ultrasonic wave radially inward as shown by arrows 104 in FIGS. 11, 12. As described previously, the laminated piezoelectric material 16 is formed to have sinusoidal ripples 48 to emit ultrasonic waves at a desired frequency. The cylindrically shaped ultrasonic transducer 98 may be attached to an inside surface 106 of housing 100 as shown in FIG. 11, or on an outside surface 108 of housing 100 as shown in FIG. 12. Generally, where the laminated piezoelectric material 16 is mounted on the outside surface 108, FIG. 12, the thickness of housing 100 is preferably minimal. In the embodiment of FIGS. 11 and 12, the preferred way of adhering the laminated piezoelectric material 16 to housing 100, and maintaining its shape, is with the use of adhesive on each sinusoidal peak in contact with housing 100 as indicated with reference numeral 110.

Figure 13:
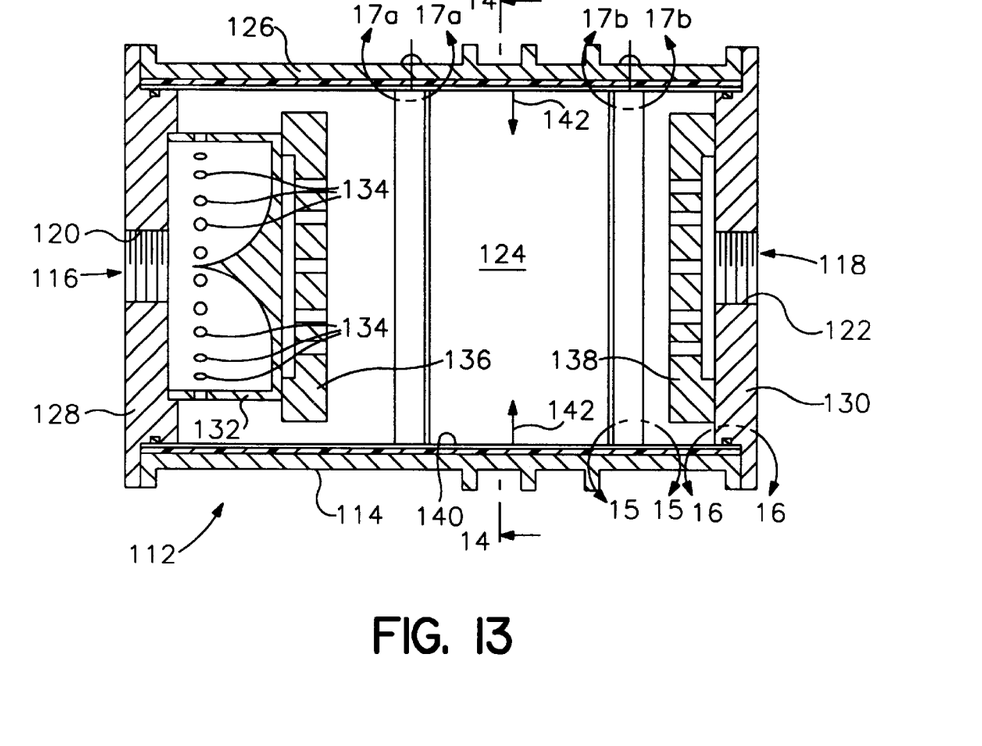
FIG. 13 is a side cross-section of a gas analyzer incorporating the present invention.

FIG. 13 shows a gas analyzer 112 which is one application for the aforementioned ultrasonic transducers. It is to be understood at the outset, that the housing shown is merely for illustration purposes and the invention is not limited to the embodiment shown. Gas analyzer 112 has a housing 114 with a gas inlet 116 and a gas outlet 118, each having a threaded passage 120 and 122, respectively, for accepting gas piping. Gas analyzer 112 has an internal chamber 124 in gaseous communication with gas inlet 116 and gas outlet 118. Housing 114 is made up of a longitudinal cylinder 126 and end caps 128 and 130 having gas inlet 116 and gas outlet 118 respectively therein. A gas flow diverter 132 is mounted in end cap 128 to direct the gas flow outwardly through a series of openings 134. A pair of sound absorbers 136 and 138 are situated at both ends of the internal chamber 124 and provide acoustical vibration absorption. The ultrasonic transducer of the present invention 140 is arranged in the internal chamber 124 of the housing 114.

In operation, gas enters gas inlet 116, is directed by the gas flow diverter 132 through the series of openings 1 34, and flows across the ultrasonic transducer 140 to the internal chamber 124. An ultrasonic emission from the ultrasonic transducer 140 converges radially inward in the internal chamber 124, as shown by arrows 142, toward a center of the internal chamber 124. The gas exits the chamber 124 through sound absorber 138 and gas outlet 118.

Accordingly, the present invention includes a method of analyzing gas including the steps of passing the gas to be analyzed through an inside surface of a cylindrical shaped ultrasonic transducer 140, energizing the transducer and radiating an ultrasonic cylindrical wave into the passing gas toward a center of the cylindrical shape transducer. The ultrasonic wave is deformed and thereby detects characteristics of the gas and is reflected outward once reaching a pressure center within the internal chamber 124. The method also includes sensing a reflected ultrasonic cylindrical wave containing acoustical characteristics indicative of the detected characteristics of the gas within the cylindrically shaped ultrasonic transducer 140, and generating an acoustical characteristic signal from the sensed ultrasonic wave.

Figure 14:
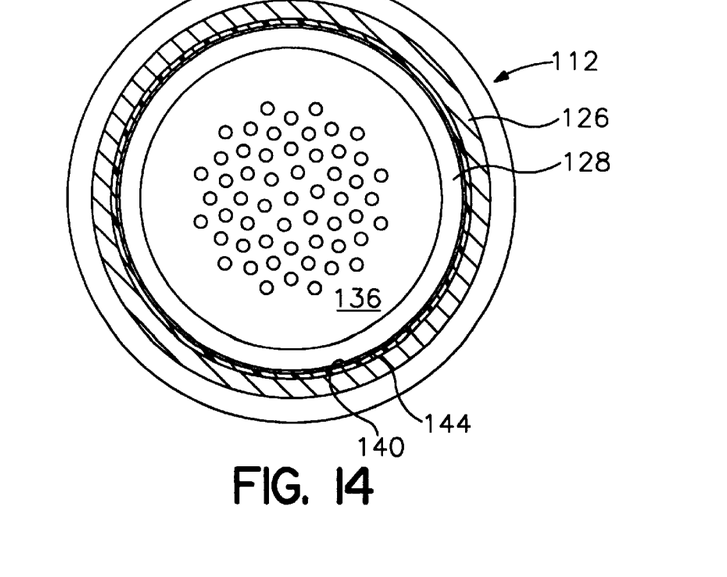
FIG. 14 is a cross-sectional view of a portion of FIG. 13 taken along line 14—14 of FIG. 13.

FIG. 14 shows a cross section of the gas analyzer 112 taken along line 14—14 of FIG. 13. The longitudinal cylinder 126 and end cap 128 are shown forming housing 114. A composite layer 144 is provided between the ultrasonic transducer 140 and cylinder 126 which also provides acoustic damping. A front face view of the sound absorber 136 is also shown in FIG. 14.

Figure 15:
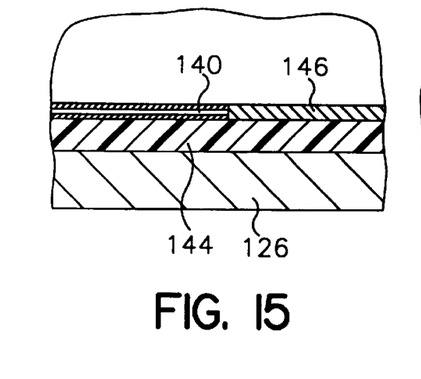
FIG. 15 is a partial sectional view of FIG. 13 taken along line 15—15 of FIG. 13.

FIG. 15 shows a detailed sectional view taken along line 15—15 in FIG. 13 showing ultrasonic transducer 140 mounted in the cylinder 126 with the composite layer 144 therebetween. Spacer 146 maintains the position of the ultrasonic transducer 140.

Figure 16:
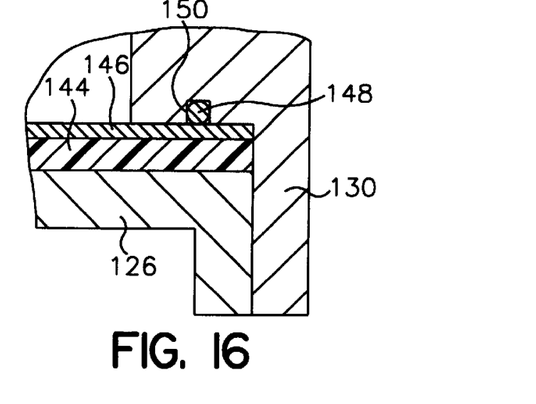
FIG. 16 is a partial sectional view of FIG. 13 taken along line 16—16 of FIG. 13.

FIG. 16 shows a detailed sectional view taken along line 16—16 of FIG. 13 in which end cap 130 is shown mounted to cylinder housing 126. The composite layer 144 runs the length of cylinder 126 and an O-ring 148 in passage 150 seals the structure between end cap 130 and spacer 146.

Figure 17A:
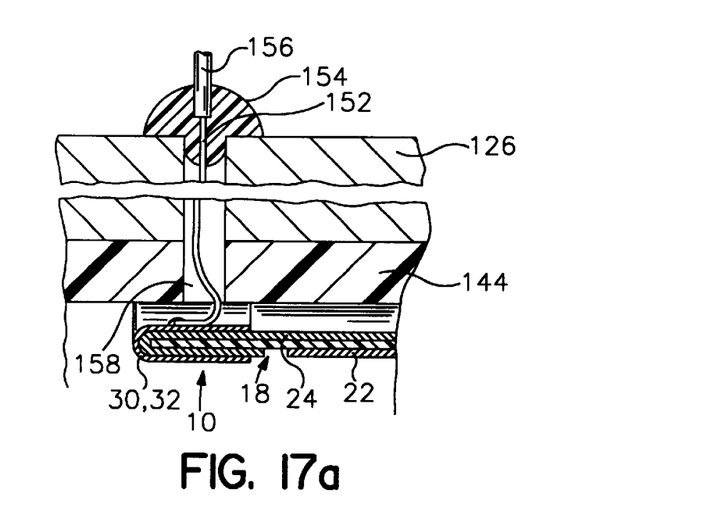
FIG. 17(a) is a partial sectional view of FIG. 13 taken along line 17a—17a of FIG. 13.
Figure 17B:
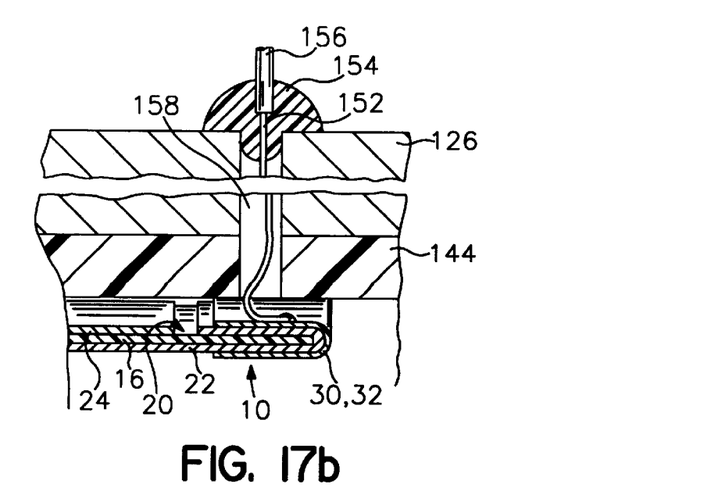
FIG. 17(b) is a partial sectional view of FIG. 13 taken along line 17b—17b of FIG. 13.

FIGS. 17(a) and (b) show details taken along lines 17a—17a and 17b—17b of FIG. 13. The ultrasonic transducer 10 is shown constructed as described with reference to FIGS. 1–6, having piezoelectric material 16 and electrically conductive metal layers 22 and 24 forming gaps 18 and 20. End caps 30 and 32 are placed on the outer edges. In this embodiment, end caps 30 and 32 are electrically conductive and electrical lead wire 152 is therefore soldered directly to the end caps and exits longitudinal cylinder 126 through openings 158. Insulators 154 are provided in openings 1 58 and lead wire 152 is connected to the insulated wire 156.

Figure 18:
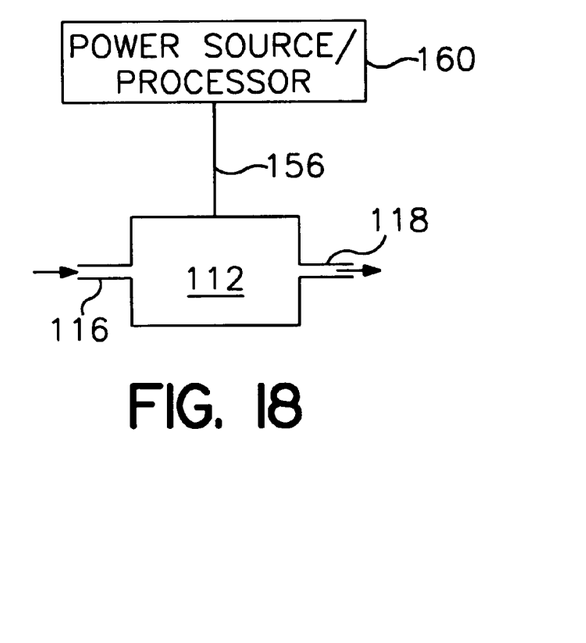
FIG. 18 is a block diagram incorporating the device of FIG. 13 in a system of the present invention.

As shown in block diagram form in FIG. 18, the gas analyzer 112 receives gas in gas inlet 116 and discharges gas through outlet 118. The analyzer 112 is connected to a processor 160 via the connections 156. Processor 160 acts as a power source in exciting the ultrasonic transducer within gas analyzer 112 and processes the return signals sensed by the ultrasonic transducer. When an electrical excitation pulse, or group of pulses, is applied to the ultrasonic transducer, it generates an acoustical wave directed radially inward having a cylindrical wave front. Once the wave converges at, or near, the center axis of the internal chamber of the gas analyzer 112, a high pressure center will reflect the wave back to the transducer. The reflected acoustical wave thereby generates an electrical signal within the transducer which is returned to the processor 160. The transmitting and receiving timing of these signals can be used to determine the time-of-fly of the acoustical wave pulse which can be calculated from the velocity of sound and the known transducer diameter. The sonic velocity in a mixture of two known gaseous components can then be used to calculate the composition of the gas as is well known and beyond the scope of this invention.

In the most general sense, this invention discloses an ultrasonic device for producing a radially inward directed ultrasonic wave having a means for emitting an ultrasonic wave of a desired frequency and for sensing a return ultrasonic wave. The emitted ultrasonic wave is directed radially inward from the means for producing the wave. The returned ultrasonic wave is reflected from a pressure center formed near the center of the ultrasonic device created by the original inwardly directed ultrasonic wave. The device includes a means for exciting the ultrasonic wave emitting means and for processing the sensed returned ultrasonic wave to determine characteristics thereof. The means for emitting an ultrasonic wave includes multiple ripple means therein for emitting a ultrasonic wave of a desired frequency.

Figure 19:
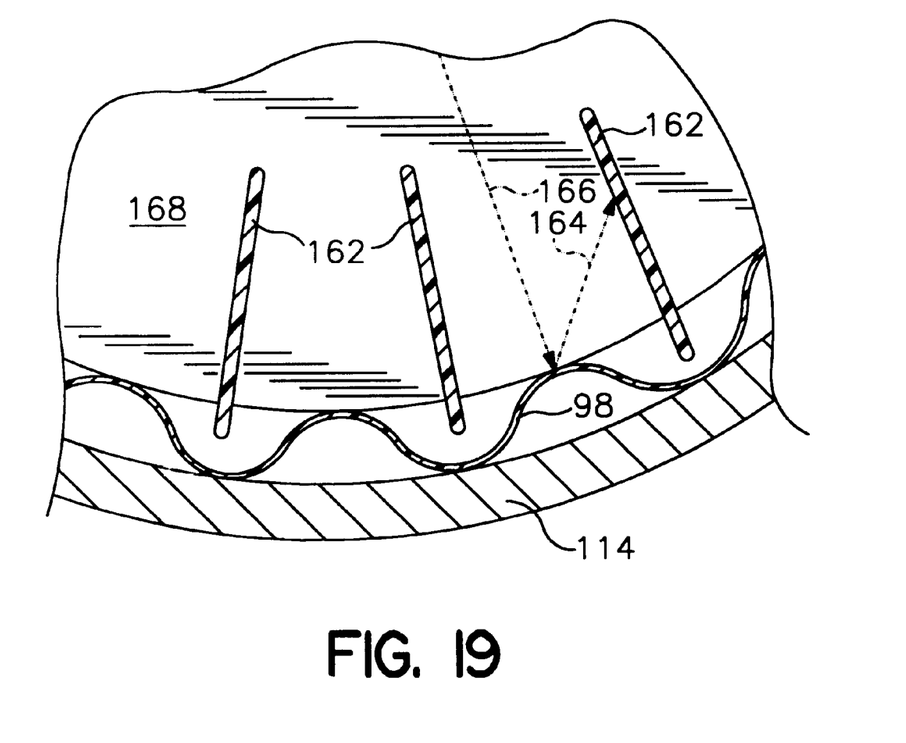
FIG. 19 is detailed cross-sectional view of a portion of FIG. 13 incorporating a plurality of ultrasound baffles.

FIG. 19 shows an alternate embodiment of the present invention in which a plurality of ultrasound baffles 162 are arranged along a periphery of the cylindrical ultrasonic transducer 98. Each of the ultrasound baffles 162 is arranged to intercept and attenuate stray ultrasonic waves as shown by dash line 164. This allows a cleaner cylindrical mode, or radial mode, ultrasonic wave to transmit radially inward as shown by dash lines 166. The plurality of ultrasonic baffles 162 are mounted to a back plain 168 which can be an end cap such as end cap 130 shown in FIG. 13. Each of the ultrasound baffles 162 are constructed of a plastic having a plurality of holes therein. This construction is known to absorb and attenuate the stray ultrasonic waves.

The present invention has been thoroughly described herein as applied in one particular gas analyzer. However, it is understood that the invention is well suited for use in many various ultrasound applications and is not limited to the application described herein and shown in the drawings.

The present invention has been described in terms of the preferred embodiments, and it is recognized that equivalents, alternatives, and modifications, aside from those expressly stated, are possible and within the scope of the appending claims.

We claim:

1. An ultrasonic transducer device for producing an inwardly directed ultrasonic wave comprising a cylindrically shaped means having a plurality of ripples therein for emitting an ultrasonic wave of a desired frequency and for sensing a returned ultrasonic wave, the emitted ultrasonic wave being directed radially inward from the cylindrically shaped means for emitting, and the returned ultrasonic wave being reflected by a pressure center formed by the inwardly directed ultrasonic wave.

2. The device of claim 1 further comprising a means for exciting the ultrasonic wave emitting means and for processing the sensed returned ultrasonic wave to determine characteristics thereof.

3. The device of claim 1 wherein the means for emitting has a plurality of ripple means therein for emitting an ultrasonic wave radially inward of the desired frequency.

4. An inwardly directed wave mode ultrasonic transducer comprising:
   a strip of piezoelectric material having inside and outside surfaces and two edge surfaces;
   a pair of electrically conductive metal layers, each metal layer placed on the inside surface and on the outside surface and spaced apart to form a gap on each surface between the pair of electrically conductive metal layers, the gaps running parallel with one another along a perimeter of the strip of piezoelectric material;
   a pair of end caps attached at each edge surface; and
   wherein the transducer is constructed substantially cylindrically and having a plurality of ripples therein to create and maintain a hollow center and is capable of radiating an ultrasonic wave radially inward from the transducer.

5. The transducer of claim 4 wherein each electrically conductive metal layer is placed such that a relatively narrow layer covers a minority of one side of the piezoelectric material and a relatively wide layer covers a majority of another side of the piezoelectric material.

6. The transducer of claim 4 wherein a single pair of electrically conductive metal layers cover the inside and outside surfaces of the strip of piezoelectric material such that a first electrically conductive material layer covers a minority of a first side of the piezoelectric material and a majority of a second side of the piezoelectric material, and a second electrically conductive metal layer covers a minority of the first side of the piezoelectric material and a majority of the second side, and wherein each electrically conductive metal layer is an electrode of the transducer.

7. The transducer of claim 4 wherein the transducer is cylindrically shaped and comprises a plurality of ripples orientated parallel to a central axis of the cylindrical shaped transducer.

8. The transducer of claim 7 wherein the ripples are continuous along a circumference of the transducer, are substantially sinusoidally shaped, and define an operational frequency of the transducer.

9. The transducer of claim 4 wherein the end caps provide stability to the transducer and are electrically conductive to conductively connect the piezoelectric material to an energy source.

10. The transducer of claim 4 wherein the end caps are rigid to maintain a desired shape and are attached over the edge surfaces by crimping, and the piezoelectric material is composed of PVDF.

11. The transducer of claim 4 further comprising a housing having a gas inlet, a gas outlet, and an internal chamber wherein the transducer is mounted for radiating ultrasonic waves radially inward toward a center of the housing where the ultrasonic waves converge near the center of the housing and reflect back to the transducer carrying characteristics of a passing gas to be detected by the piezoelectric material.

12. The transducer of claim 11 wherein the housing further comprises a gas inlet diverter situated near the gas inlet to direct the flow of gas through the internal chamber and across the transducer.

13. The transducer of claim 11 further comprising an energy source and processor electrically connected to the piezoelectric material to induce an ultrasonic wave toward a center of the transducer and process the detected characteristics.

14. An ultrasonic transducer comprising:
   a strip of piezoelectric material having a pair of electrically conductive metal layers on an inside surface and an outside surface such that each is electrically isolated from one another;
   a nonconductive mesh cage having a plurality of vertical members, a plurality of horizontal members, and a plurality of vertical openings between the plurality of vertical members wherein the strip of piezoelectric material is weaved therebetween; and
   wherein the transducer is constructed substantially cylindrically and having a plurality of ripples therein to create and maintain a hollow center and is capable of radiating an ultrasonic wave radially inward.

15. The transducer of claim 14 having a substantially cylindrical shape and wherein the ultrasonic wave generated thereby is substantially cylindrical in shape.

16. The transducer of claim 14 wherein a spatial frequency of the vertical members and the vertical openings in the nonconductive mesh define an operational frequency of the transducer.

17. The transducer of claim 14 wherein the weaved strip of piezoelectric material creates a substantially sinusoidal shape that defines an operational frequency of the transducer.

18. The transducer of claim 14 wherein the nonconductive mesh is nonmetallic.

19. A method of producing an ultrasonic transducer comprising the steps of:
   determining a modulus of elasticity and density of a piezoelectric material;
   determining a desired operating frequency of the ultrasonic transducer;
   calculating an optimal radius of a sinusoidal ripple based on the modulus of elasticity and the density of the piezoelectric material and the desired operating frequency; and shaping the piezoelectric material to form a continuous full wave sinusoid, wherein each half-wave of the sinusoid has a radius substantially equal to the calculated optimal radius.

20. The method of claim 19 further comprising the steps of:

acquiring a pair of geared rollers having a tooth pitch and diameter based on the calculated optimal radius;

arranging the pair of geared rollers such that the teeth of one geared roller mesh with the teeth of the other geared roller in close relation and controlled distance; and wherein the step of shaping is further defined as feeding the piezoelectric material through the meshed pair of geared rollers to form the continuous full wave sinusoid.

21. The method of claim 19 further comprising the steps of:

acquiring a nonconducting mesh cage having vertical members, horizontal members, and vertical openings in the horizontal members; and wherein the step of forming is further defined to include threading the piezoelectric material through the vertical openings and between the vertical members to form the continuous full wave sinusoid.

22. The method of claim 19 further comprising the step of connecting each end of the piezoelectric material to form a substantially cylindrically shaped ultrasonic transducer.

23. The method of claim 19 further comprising the step of attaching a pair of end caps to the edges of the piezoelectric material to provide rigidity to the transducer.

24. The method of claim 19 further comprising the step of adhering the piezoelectric material to a substantially cylindrical housing to provide rigidity to the transducer.

25. The method of claim 24 wherein the step of adhering is defined as adhering a peak if each full wave sinusoid to the housing.

26. A method of analyzing gas comprising the steps of:

passing a gas to be analyzed through an inside surface of a substantially cylindrical shaped ultrasonic transducer having periodic ripples therein;

energizing the substantially cylindrically shaped ultrasonic transducer;

radiating an ultrasonic cylindrical wave into the passing gas and toward a center of the substantially cylindrically shaped ultrasonic transducer wherein the ultrasonic cylindrical wave detects characteristics of the gas; and sensing a reflected ultrasonic cylindrical wave containing acoustical characteristics indicative of the detected characteristics of the gas with the substantially cylindrically shaped ultrasonic transducer.

27. The method of claim 26 further comprising the step of generating an acoustical characteristics signal from the reflected ultrasonic cylindrical wave.

28. The method of claim 27 further comprising the step of processing the acoustical characteristic signal to determine the detected characteristics of the gas.

29. A gas analyzer comprising a housing having a gas inlet, a gas outlet, and an internal chamber in gaseous communication with the gas inlet and gas outlet; and a cylindrical ultrasonic transducer having a series of ripples therein, a hollow center, and arranged in the internal chamber of the housing to allow a flow of gas therethrough, and wherein an ultrasonic emission from the ultrasonic transducer converges radially inward toward a center of the internal chamber.

30. The gas analyzer of claim 29 further comprising a processor for exciting the ultrasonic transducer and processing an acoustical characteristic signal generated by a reflected ultrasonic wave sensed by the ultrasonic transducer.

31. The gas analyzer of claim 29 wherein the ultrasonic transducer comprises:

a strip of piezoelectric material formed in a substantially cylindrical shape having inside and outside surfaces, two edge surfaces, and a series of ripples therein;

a pair of electrically conductive metal layers placed on the inside surface and on the outside surface and spaced apart to form a gap on each surface between the pair of electrically conductive metal layers, the gaps running parallel with one another along a perimeter of the cylindrically shaped strip of piezoelectric material;

a pair of end caps attached at each edge surface of the cylindrical shaped transducer; and wherein the transducer is constructed to create and maintain a hollow center and is capable of radiating a substantially cylindrical ultrasonic wave radially inward from the ultrasonic transducer.

32. The gas analyzer of claim 31 wherein each electrically conductive metal layer is placed such that a relatively narrow layer covers a minority of one side of the piezoelectric material and a relatively wide layer covers a majority of another side of the piezoelectric material.

33. The gas analyzer of claim 31 wherein the cylindrically shaped transducer comprises a plurality of ripples orientated parallel to a central axis of the cylindrical shaped transducer.

34. The gas analyzer of claim 29 wherein the ultrasonic transducer comprises:

a strip of piezoelectric material having a pair of electrically conductive metal layers on an inside surface and an outside surface such that each is electrically isolated from one another;

a nonconductive mesh cage having a plurality of vertical members, a plurality of horizontal members, and a plurality of vertical openings between the plurality of vertical members wherein the strip of piezoelectric material is weaved therebetween; and wherein the transducer is constructed to create and maintain a hollow center and is capable of radiating an ultrasonic wave radially inward.

35. The gas analyzer of claim 34 wherein the transducer has a substantially cylindrical shape and wherein the ultrasonic wave generated thereby is substantially cylindrical in shape, and a spatial frequency of the vertical members and the vertical openings in the nonconductive mesh cage define an operational frequency of the transducer.

36. The gas analyzer of claim 29 further comprising an energy source electrically connected to the piezoelectric material to induce an ultrasonic wave toward a center of the transducer, and wherein the housing is capable of passing a gas therethrough and the ultrasonic wave converges near the center of the transducer and reflects back to the transducer carrying characteristics of the gas to be detected by the piezoelectric material.

* * * * *